United States Patent [19]

Baganz et al.

[11] 3,966,757

[45] June 29, 1976

[54] IMIDAZOLINE DERIVATIVES AND PROCESSES FOR THE PRODUCTION THEREOF

[75] Inventors: Horst Baganz, Moorrege; Hans-Joachim May, Neustadt-Hambach, both of Germany

[73] Assignee: A. Nattermann & Cie GmbH, Germany

[22] Filed: Apr. 8, 1975

[21] Appl. No.: 566,136

Related U.S. Application Data

[63] Continuation-in-part of Ser. No. 440,345, Feb. 7, 1974, abandoned, which is a continuation of Ser. No. 164,815, July 21, 1971, abandoned, which is a continuation of Ser. No. 706,665, Feb. 19, 1968, abandoned.

[30] Foreign Application Priority Data

Feb. 23, 1967 Germany.............................. 30055

[52] U.S. Cl......................... 260/309.6; 260/309.7; 260/453 R; 260/465 F; 260/500.5 H; 260/502.6; 260/564 R; 424/273

[51] Int. Cl.²........................................... C07D 49/34
[58] Field of Search.................................. 260/309.6

[56] References Cited
UNITED STATES PATENTS

| | | | |
|---|---|---|---|
| 2,516,108 | 7/1950 | Djerassi et al................... | 260/309.6 |
| 3,449,355 | 6/1969 | White.............................. | 260/309.6 |
| 3,449,357 | 6/1969 | White.............................. | 260/309.6 |
| 3,897,431 | 7/1975 | Bailey............................ | 260/251 R |

OTHER PUBLICATIONS

C.A. 70:68371x.
C.A. 74:87979a.
Scholz, Industrial and Engineering Chem., vol. 37 (1945), pp. 120–125.

*Primary Examiner*—Ethel G. Love
*Attorney, Agent, or Firm*—McNenny, Pearne, Gordon, Gail, Dickinson & Schiller

[57] ABSTRACT

2-[α-(2,6-dichlorophenoxy)-ethyl]-Δ²-imidazoline, and physiologically acceptable acid addition salts thereof, which provide vasoactivity and hypotensive activity.

2 Claims, No Drawings

IMIDAZOLINE DERIVATIVES AND PROCESSES FOR THE PRODUCTION THEREOF

BACKGROUND AND SUMMARY OF INVENTION

This application is a continuation-in-part of our copending application Ser. No. 440,345 filed Feb. 7, 1974, now abandoned, which is in turn a continuation of our then copending application Ser. No. 164,815 filed July 21, 1971, now abandoned, and which was in turn a continuation of our then copending application Ser. No. 706,665 filed Feb. 19, 1968, now abandoned.

The present invention relates to a new imidazoline derivative 2-[α-(2,6-dichlorophenoxy)-ethyl]-Δ²-imidazoline having the formula (I)

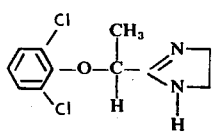
(I)

and their acid addition salts. This compound is useful particularly in view of its vasoactivity and anti-hypertensive activity. The invention is further related to processes for the production of the new compound by reacting an aryloxy carboxylic acid of the general formula (II)

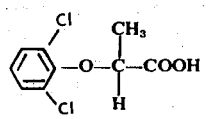
(II)

with ethylene diamine or certain derivatives thereof thus forming the imidazoline ring.

There is in existence a series of imidazoline derivatives that are substituted in the 2-position by aryloxyalkyl groups incorporating a linear alkyl group. These compounds are distinguished in particular by their vasoconstrictive, spasmolytic and antihistaminic activity.

It is an object of the present invention to provide new and useful imidazoline derivatives having improved pharmacological properties.

Other objects of the present invention and advantages thereof will become apparent as the description proceeds.

It has now been found that the novel, hitherto unreported aryloxyisoalkyl imidazoline corresponding to the formula (I)

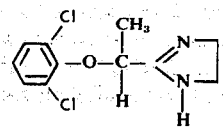
(I)

and its acid addition salts are distinguished by novel unexpected pharmacological properties and, most unexpectedly, the presence of both vasoconstrictive and hypotensive activity. The compound of the present invention has useful anti-hypertensive activity in mammals, rats and humans. The compound according to the invention may be used as a pharmaceutical agent.

The new compound and its acid addition salts, particularly with physiologically or pharmacologically acceptable acids, may be prepared by a process which is described below.

The aryloxycarboxylic acid corresponding to the formula (II)

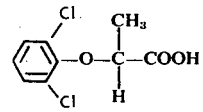
(II)

or one of its functional acid derivatives, may be used as starting material. A compound of this group is reacted either with ethylene diamine corresponding to the formula (III)

$$H_2N-CH_2-CH_2-NH_2 \quad (III)$$

or with ammonia or ammonia donors and a compound that can be converted into the ethylene diamine by treatment with ammonia. The new imidazoline derivative of formula (I) is formed either directly or in stages during these reactions.

Suitable functional acid derivatives include for example esters, orthoesters, acid halides, preferably the acid chlorides, amides, thioamides, amidines, imido-acid esters, thio-imido-acid esters, imino halides or the nitriles of the corresponding aryloxyisoalkyl carboxylic acids. The reaction may also be carried out under such conditions that the functional acid derivatives are only formed during the reaction.

In addition to the ethylene diamine itself, reactive N-derivatives of this ethylene diamine may also be used. Preferred N-derivatives of this ethylene diamine include those which give imidazolines when reacted with carboxylic acids or their functional derivatives. Examples of compounds such as these include N-acyl-ethylene diamine, N,N'-diacyl-ethylene diamines or ethylene urea.

Examples of compounds that can be converted into the ethylene diamine by treatment with ammonia or into N-monosubstituted ethylene diamines by treatment with amines of the formula $R_4NH_2$ include amino-ethanol or its esters β-halogenethylamines such as β-chloroethylamines, ethylene dihalides such as 1,2-dichloroethane or ethylene chlorohydrin. Ethylene diamine or its derivatives may be used either in the form of free bases or in the form of their mono- or di-salts in quantities corresponding to 0.8–1.2-times the stoichiometric quantity. For example, the ethylene diamine may be used in the form of its mono-p-toluene sulphonic acid salt.

In cases where the nitrile of the corresponding aryloxyisoalkyl carboxylic acid is used as the starting material and reacted with the ethylene diamine or its derivatives, it is of advantage to conduct the reaction in the presence of hydrogen sulphide or hydrogen sulphide donors such as for example carbon disulphide.

The reactions described may lead either directly or in stages to the imidazoline derivative of formula (I). For example, a compound corresponding to the formula (IV)

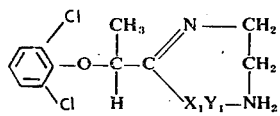

(IV)

in which $X_1 = $ OH, SH or $NH_2$ and $Y_1 = $ H or acyl, may be formed as intermediate. The substituents $X_1$ and $Y_1$ may be eliminated as $X_1Y_1$ from compounds of this type or from their tautomeric forms by methods known per se. For example, water can be eliminated from a compound of formula (IV) in which $X_1 = $ OH and $Y_1 = $ H, using calcium oxide as the dehydrating agent. In this case, the corresponding imidazoline derivative of formula (I) is formed in a high yield.

A compound of the formula (V)

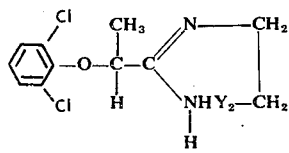

(V)

in which $Y_2$ represents a group that can be substituted by an amino group, may also be formed as intermediate. The group $Y_2$ may be eliminated in the form of $HY_2$ from a compound of this type or from its tautomeric form, in which case the imidazoline ring is formed. Intermediate products of this type are relatively unstable compounds which, when simply boiled in a suitable inert solvent, are converted into the required imidazoline compound of formula (I), accompanied by the elimination of $HY_2$. The cleavage reaction is particularly smooth in cases where $Y_2 = $ halogen. However, the reactions also produce good yields where $Y_2 = $ OH and where they are carried out under dehydrating conditions.

Compounds corresponding to the formula (VI)

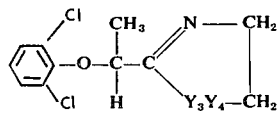

(VI)

in which $Y_3$ and $Y_4$ are the same or different and represent groups that can be substituted by an amino group such as halogen for example, may also be used as intermediates in cases where the imidazoline derivatives are formed in stages. If a compound of this type or its tautomeric form is treated with ammonia or ammonia donors, the imidazoline derivatives of formula (I) are obtained. The reaction is particularly smooth where $Y_3$ and $Y_4$ represent halogen, chlorine in particular.

It is also possible to prepare the novel imidazoline derivative of formula (I) by other known methods, for instance by decarboxylating a compound of the formula (VII)

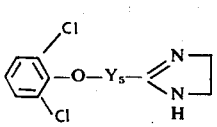

(VII)

in which $Y_5$ represents the group

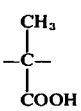

The aforementioned groups may be converted into a

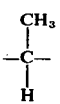

group by decarboxylation. Decarboxylation is best carried out under heat, for example by heating the hydrochloride or the p-toluene sulphonic acid salt to around 200°–250°C. It is of advantage in this case to operate in the presence of a high-boiling solvent.

The new imidazoline derivative of formula (I) may also be prepared from compounds corresponding to the formula (VIII)

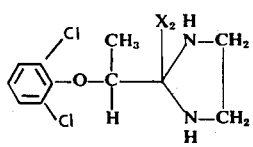

(VIII)

in which $X_2$ represents a hydroxy-, alkoxy- or acycloxy- group, preferably a lower alkoxy group, or a halogen atom, by eliminating the radical $X_2$ in the form of $HX_2$. Where $X_2$ represents halogen, elimination is carried out under the conditions normally used for the elimination of hydrogen halides, for example by treatment with collidine or pyridine. Where $X_2$ represents hydroxyl, elimination is carried out by treatment with a dehydrating agent. Where $X_2$ represents the ester radical of an aromatic or higher aliphatic carboxylic acid, for example the benzoyloxy radical, it is possible simply by heating to incorporate the 1,2-double bond in the heterocyclic radical accompanied by the elimination of benzoic acid.

It is still furthermore possible to obtain the imidazoline derivative of formula (I) by isomerizing a compound of formula (IX) or (X)

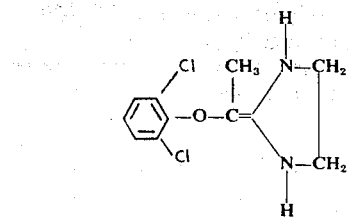
(IX)

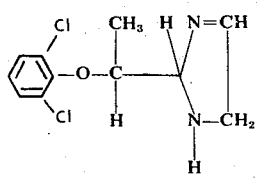
(X)

The double bond starting from the second carbon atom in the compound of formula (IX), or the double bond in the 3,4-position in the compound of formula (X) is displaced during this reaction into the 2,3-position. Isomerization reactions of this kind are preferably carried out in aqueous acid solution, for example in the presence of a small excess of HCl. Isomerization is initiated either by leaving the reaction mixture standing at room temperature or by gently heating the reaction solution.

The novel imidazoline derivative is further obtained either in the form of a free base or in the form of one of their acid addition salts, depending upon the type of method used. A variety of acid addition salts can be prepared by conventional methods from the free base by treating them with acids.

Acids of the kind that give physiologically or pharmacologically acceptable acid addition salts may be used in the preparation of these salts, examples including hydrohalic acids, in particular hydrochloric acid, sulphuric acid, orthophosphoric acid, alkane carboxylic acids such as acetic acid or propionic acid, polybasic acids such as for example oxalic acid, tartaric acid, succinic acid, maleic acid, ascorbic acid or citric acid, sulphonic acid such as methane sulphonic acid, ethane sulphonic acid, benzene sulphonic acid or p-toluene sulphonic acid, aromatic carboxylic acids such as benzoic acid, salicyclic acid or p-aminosalicyclic acid.

The new imidazoline derivative obtained in accordance with the invention and its acid addition salts may be converted into any form of pharmaceutical preparation, optionally with the aid of the usual auxiliaries.

In addition to the properties which this class of compounds is known to have, for example their antihistaminic and spasmolytic activity, the novel imidazoline derivative also shows inter alia local anaesthetic and sympathomimetic properties with specific activity on the heart. In particular, the new compound is vasoactive and may be used partially as a vasoconstrictor and partially as an agent to stop or decrease the swelling of mucous membranes in the form of nose drops or nose sprays.

Further, the new compound of the present invention has been found to have surprisingly high anti-hypertensive activity. Orally administered, a dosage of from about 100 μg to about 500 μg of the compound of formula I free base or the equivalent amount of its salt, the usual dosage is from 100 μg to 500 μg e.g. 300 μg, 450 μg, is effective. Upon comparison with structurally similar prior art compounds, they were found to be inactive or at best one-tenth as active with respect to hypotensive activity as compared to the compound of the present invention as described below in greater detail.

The preparation of the novel compound of general formula (I) and the use thereof is described more fully in the following Examples.

EXAMPLE 1 a. α-(2,6-dichlorophenoxy)-propionitrile 100 ml. Of dry ethylmethyl ketone are added to 32.6 g. of 2,6-dichlorophenol, 26 g. of anhydrous, finely powdered potassium carbonate and 0.5 g. of potassium iodide. A solution of 29.5 g. of α-bromopropionitrile in 20 ml. of absolute ethyl methyl ketone is added dropwise over 1½ hrs. to the resulting vigorously stirred suspension as it boils under reflux. On completion of the addition, the reaction mixture is heated under reflux for another hour, after which it is separated on cooling from the insoluble components present in it by filtration under suction, the residue washed with ethylmethyl ketone and the filtrate concentrated by evaporation in vacuo. Ether is added to the oily residue, the ethereal solution extracted three times with 50 ml. of 10% sodium hydroxide in order to remove the excess 2,6-dichlorophenol, and then with 50 ml. of 5% sodium thiosulphate solution in order to remove the iodine. The product is then washed with water until it reacts neutrally and dried over anhydrous sodium sulphate. After the solvent has been removed, fractionation of the residual oil in a high vacuum gives 31 g. of α-(2,6-dichlorophenoxy)-propionitrile.

Yield: 71.5% of the theoretical. White needles M.p. 28° – 29° b. α-(2,6-dichlorophenoxy)-propionimidoacid ethyl ester hydrochloride 10.4 ml. Of absolute ethanol are added to 57.5 g. of α-2,6-dichlorophenoxypropionitrile, followed by the introduction of 100 ml. of chloroform dried over phosphorus pentoxide, 10.4 g. of carefully dried hydrogen chloride being slowly introduced with stirring and cooling with ice/common salt. Most of the chloroform and excess hydrogen chloride is then removed by filtration in vacuo at room temperature, and dry ether added to the residue until the imidoacidester hydrochloride is quantitatively precipitated. The α-dichlorophenoxy-propionimidoacid ethyl ester hydrochloride can be obtained analytically pure in the form of white, strongly, hygroscopic crystals by repeated dissolation in a little absolute ethanol in the absence of heat, and precipitation with ether.

The crude product of the α-(2,6-dichlorophenoxy)-propionimidoacid ethyl ester hydrochloride is sufficiently pure for further reactions, even without precipitations with ether beforehand.

c. 2-[α-(2,6-dichlorophenoxy)-ethyl]-Δ²-imidazolidine hydrochloride

The crude α-(2,6-dichlorophenoxy)-propionamido-acid ethyl ester hydrochloride is added in portions to a stirred, ice-cooled solution of 29.5 g. of anhydrous ethylene diamine in 200 ml. of absolute ethanol in such a way that the temperature does not exceed 0° to 5°C. The cooling bath is then removed and the reaction mixture heated for 1 hour on a water bath to approximately 70°C. After cooling, unreacted ethylene diamine is neutralized in a cooling mixture with absolute ethanolic hydrochloric acid, filtered off from any components that are insoluble in ethanol and approximately two-thirds of the solvent filtered off under suction in a water jet pump vacuum. Residual quantities of ethylene diamine dihydrochloride are precipitated in fractions by the careful addition of ethylmethyl ketone, after which the imidazoline hydrochloride is separated off by the addition of dry ether. Following repeated recrystallization from ethanol ether, 2-[α-(2,6-dichlorophenoxy)-ethyl]-Δ²imidazoline hydrochloride is obtained in the form of small white crystals melting at 221° – 223°C.

ANALYSIS: $C_{11}H_{13}Cl_3N_2O$ (295.6). Calculated: N, 9.48; Cl, 35.99. Found: N, 9.46; Cl, 36.01.

EXAMPLE 2

Tablets

Tablets are produced by mixing an appropriate binder and usual additives and the compound obtained according to Example 1 in such amounts that each tablet contains 0.15 mg. of the active compound.

EXAMPLE 3

Nose drops

A 0.1 percent solution of the compound obtained according to Example 1 in a physiological sodium chloride solution is produced and may be used as nose drops.

EXAMPLE 4

A patient suffering from an influenza with snuffing and strongly enhanced breathing through the nose obtained the nose drops according to Example 1 in a dose of 2 drops each time and 3 to 5 times per day. He was able to breath substantially without enhancement about 5 minutes after the administration. Breathing through the nose was undisturbed for about 5 hours. No undesired side effects were observed even after a regular administration through 9 days.

The anti-hypertensive activity of the compound of formula I was compared with that of two other prior art compounds having a chemically similar structure as summarized in Table I. The hydrochloride salt of each compound is compared with respect to hypotensive activity in male Wistar rats which were anesthetized with 1.5 g. of Urethane/kg intraperitoneal.

The compounds to be compared were injected slowly (e.g. about 45 seconds) into the left jugular vein in the form of a solution at the reported dosage and concentration in a 0.9% saline solution. The right A. carotis was connected to a blood pressure transducer and recorder for measurement of systolic blood pressure. The initial blood pressure in all of the animals used averaged 119.7 mm Hg ± 12.5 (standard deviation).

The maximum decreases in blood pressure are tabulated in Table I in terms of the absolute values (mm Hg), the percent of the decreases are indicated, and the time of the activity is reported in minutes. All of the compounds were evaluated at a dosage of 10 μg/kg. In addition, the compound of formula I, (Compound A), was tested at a dosage of 1 μg/kg and the prior art related compounds, (Compounds B and C), were tested at a dosage of 100 μg/kg. Compound B is known as 2-[(2′,6′-dichlorophenoxy) methyl]-Δ²-imidazoline hydrochloride, and Compound C is known as 2-[(3′,4′-dichlorophenoxy)methyl]-Δ²-imidazoline hydrochloride.

TABLE I

| Dosage (μg/kg) | COMPOUND A Change (mm Hg) | Percent Change | Duration (min) | COMPOUND B Change (mm Hg) | Percent Change | Duration (min) | COMPOUND C Change (mm Hg) | Percent Change | Duration (min) |
|---|---|---|---|---|---|---|---|---|---|
| 1 | 40 | 33.3 | 30 | | | | | | |
|  | 22 | 19.6 | 30 | | | | | | |
| 10 | 63 | 53.4 | 90 | 0 | 0 | 0 | 0 | 0 | 0 |
|  | 30 | 27.3 | 30 | 20 | 16.7 | 10 | 10 | 8.3 | 20 |
|  | 40 | 36.4 | 45 | 16 | 14.8 | 10 | 5 | 4 | 2 |
|  | 35 | 31.8 | 60 | 14 | 12.7 | 20 | 0 | 0 | 0 |
|  | 80 | 53.5 | 45 | 0 | 0 | 0 | 0 | 0 | 0 |
|  | 40 | 29.4 | 80 | 5 | 5.6 | 20 | 0 | 0 | 0 |
|  | | | | 16 | 13.3 | 10 | | | |
|  | | | | 8 | 6.3 | 20 | | | |
|  | 48.0* | 38.6* | 58.3* | 9.9 | 8.68 | 11.3 | 2.5 | 2.1 | 3.7 |
|  | ±19.3** | ±11.8** | ±23.0** | ±7.7 | ±6.6 | ±8.3 | ±4.2 | ±3.5 | ±8.0 |
| 100 | | | | 40 | 33.3 | 30 | 0 | 0 | 0 |
|  | | | | 40 | 44.4 | 30 | 15 | 0 | 30 |

COMPOUND A: 2-[α-(2,6-dichlorophenoxy)ethyl]-Δ²-imidazoline hydrochloride
COMPOUND B: 2-[(2′,6′-dichlorophenoxy)methyl]-Δ²-imidazoline hydrochloride
COMPOUND C: 2-[(3′,4′-dichlorophenoxy)methyl]-Δ²-imidazoline hydrochloride
*σ<0.001 with respect to the average values for Compounds B or C.
**Standard deviation of average values.

With reference to Table I, it is apparent that the compound of formula I provide a recognized, strong hypotensive action for a surprisingly prolonged time period at the 10 μg/kg dosage. The average decrease in blood pressure is 48 mm Hg and the effect lasted for an average period of about one hour. In contrast, Compound B displayed significant activity in only some cases and Compound C is substantially inactive. The standard deviation values are indicated below the average values in Table I, and the significance of the differences between the average values upon comparison is emphasized by a σ value of less than 0.001.

The activity of Compound A was also tested at a 1 μg/kg dosage, and a clear hypotensive activity was obtained even at this reduced dosage. Further, Compounds B and C were each tested at a 100 μg/kg dosage. Compound C remained substantially inactive at this increased dosage. Compound B is at best one-tenth as active as compared with Compound A since a tenfold increase in dosage of Compound B is required before results of the same order of magnitude as those of Compound A are obtained.

The hypotensive activity of Compound A has also been demonstrated in cats and dogs. When given in doses between 1 and 31.6 μg/kg intravenously and between 6.81 and 100 μg/kg intraduodenal to cats, as well as in doses between 1 and 6.81 μg/kg intravenously, and between 3.16 and 10 μg/kg per os to dogs, the compound showed a dose-dependent reduction of arterial blood pressure which lasted for 5 to 6 hours without reducing the supply of blood to vital organs. This effect was also proved in a chronic test in DCA-rats with artificial high blood pressure.

Clinical studies of the hypotensive activity of the compound in accordance with the formula I have also been found favorable. In double blind studies, 155 patients were treated with 300 to 450 μg of the compound of formula I orally administered for three to four weeks. A statistically significant decrease of pathologically increased blood pressure was found, and there was no evidence of orthostatic reactions. The same result was found in open field studies involving 400 patients.

Accordingly, an unexpectedly strong and markedly prolonged hypotensive activity has been found with respect to the compound of formula I, and this activity has been proven in both preclinical and clinical work. In view of the activity comparison with similar prior art compounds and the activity of the compound of formula I even at relatively low dosages (1 μg/kg in the preclinical studies), it is apparent that the activity of the compound of the present invention is closely connected to the specific chemical structure.

What is claimed is:
1. A compound having the formula

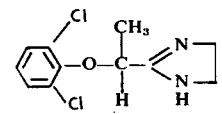

and its pharmaceutically acceptable acid addition salts.
2. A compound in accordance with claim 1 wherein the pharmaceutically acceptable salt is hydrochloride.

* * * * *